(12) United States Patent
Musa et al.

(10) Patent No.: US 10,093,633 B2
(45) Date of Patent: Oct. 9, 2018

(54) FUNCTIONALIZED 4- AND 5-VINYL SUBSTITUTED REGIOISOMERS OF 1, 2, 3-TRIAZOLES VIA 1, 3-DIPOLAR CYCLOADDITION AND POLYMERS THEREOF

(71) Applicant: ISP Investments LLC, Wilmington, DE (US)

(72) Inventors: Osama M. Musa, Bedminster, NJ (US); Brian Marr, Hampton, NJ (US)

(73) Assignee: ISP Investments LLC, Wilmington, DE (US)

(*) Notice: Subject to any disclaimer, the term of this patent is extended or adjusted under 35 U.S.C. 154(b) by 0 days.

(21) Appl. No.: 14/960,597

(22) Filed: Dec. 7, 2015

(65) Prior Publication Data

US 2016/0083356 A1 Mar. 24, 2016

Related U.S. Application Data

(62) Division of application No. 13/255,544, filed as application No. PCT/US2010/026637 on Mar. 9, 2010.

(Continued)

(51) Int. Cl.

| | | |
|---|---|---|
| *C07D 403/00* | (2006.01) | |
| *C07D 249/04* | (2006.01) | |
| *A01N 43/647* | (2006.01) | |
| *C07D 295/155* | (2006.01) | |
| *C08F 26/06* | (2006.01) | |
| *A61K 8/49* | (2006.01) | |
| *A61Q 19/00* | (2006.01) | |
| *C09D 139/04* | (2006.01) | |
| *C09J 139/04* | (2006.01) | |
| *C11D 3/28* | (2006.01) | |
| *A61K 8/81* | (2006.01) | |
| *C11D 3/37* | (2006.01) | |

(52) U.S. Cl.
CPC ......... *C07D 249/04* (2013.01); *A01N 43/647* (2013.01); *A61K 8/496* (2013.01); *A61K 8/817* (2013.01); *A61Q 19/00* (2013.01); *C07D 295/155* (2013.01); *C08F 26/06* (2013.01); *C09D 139/04* (2013.01); *C09J 139/04* (2013.01); *C11D 3/28* (2013.01); *C11D 3/3776* (2013.01); *A61K 2800/10* (2013.01)

(58) Field of Classification Search
None
See application file for complete search history.

(56) References Cited

U.S. PATENT DOCUMENTS 3,161,651 A * 12/1964 Stansbury, Jr. ...... C07D 249/04
548/255
5,315,013 A 5/1994 Carini et al.
(Continued)

FOREIGN PATENT DOCUMENTS

WO WO2004101531 A * 11/2004

OTHER PUBLICATIONS

Tsypin et al., Zhurnal Organicheskoi Khimii (1975), 11(7), 1395-400.*
Raymond et al., American Chemical Society (2006), 128(37), 12084-12085.*
Tikhonova et al., Zhurnal Organicheskoi Khimii (1981), 17(7), 1401-5.*
Tsypin et al., Zhurnal Organicheskoi Khimii (1975), 11(7), 1395-1400.*

(Continued)

*Primary Examiner* — Shobha Kantamneni
(74) *Attorney, Agent, or Firm* — William J. Davis

(57) ABSTRACT

The present invention provides novel functionalized mixtures 4- and 5-vinyl substituted regioisomers of 1,2,3-triazoles via 1,3-dipolar cycloaddition. Functionalized alkyne moieties with a terminal alcoholic functionality are reacted with functionalized organic moieties with a terminal leaving group and an azide to provide an alcoholic functionalized mixture of 4- and 5-substituted regioisomers of 1,2,3-triazole moieties. The mixture may be converted to a wide variety of useful functionalized mixtures of 4- and 5-vinyl substituted regioisomers of 1,2,3-triazole moieties, which in turn can be converted to a wide variety of useful polymers The novel alcoholic functionalized mixtures of 4- and 5-substituted regioisomers can be separated by chromatography to provide the purified 4- and 5-alcoholic functionalized substituted 1,2,3-triazole moieties. The novel compounds of the invention can be employed in a wide variety of compositions (Formulae (I), (II)); wherein $R_1$, $R_2$, $R_3$, and $R_4$, are defined herein.

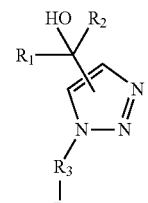

(I)

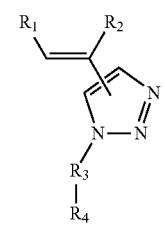

(II)

3 Claims, No Drawings

Related U.S. Application Data

(60) Provisional application No. 61/159,265, filed on Mar. 11, 2009, provisional application No. 61/159,610, filed on Mar. 12, 2009.

(56) References Cited

U.S. PATENT DOCUMENTS

| | | |
|---|---|---|
| 6,743,924 B2 | 6/2004 | Shih et al. |
| 6,914,058 B2 * | 7/2005 | Das ............... C07D 249/06 514/227.8 |
| 2005/0222427 A1 | 10/2005 | Sharpless et al. |
| 2006/0111530 A1 | 5/2006 | Li et al. |

OTHER PUBLICATIONS

Morales-Sanfrutos et al., Journal of Organic Chemistry, 2008, 73(19), 7768-7771.*
Nulwala et al., Polymer Preprints, 2007, 48(1 ), 333.
Prabahar et al., Indian Journal of Heterocyclic Chemistry (1992), 1(4), 157-70.
Wouters et al., Makromol. Chem. 183, 1861-1868, 1982.
Hawker, Jags, 1994, 116, 11185-11186.
Thibault et al. A Versatile New Monomer Family: Functionalized 4-Vinyl-1,2,3-Triazoles via Click Chemistry. Journal of American Chemical Society, 2006, 128, pp. 12084-12085.

* cited by examiner

FUNCTIONALIZED 4- AND 5-VINYL SUBSTITUTED REGIOISOMERS OF 1, 2, 3-TRIAZOLES VIA 1, 3-DIPOLAR CYCLOADDITION AND POLYMERS THEREOF

BACKGROUND OF THE INVENTION

Field of the Invention

The present invention provides novel functionalized 4- and 5-vinyl substituted regioisomers of 1,2,3-triazoles via 1,3-dipolar cycloaddition. The novel compounds are prepared by the ligation of azides and alkynes using 1,3-dipolar cycloaddition reactions. Functionalized alkyne moieties with a terminal alcoholic functionality are reacted with functionalized organic moieties with a terminal leaving group and an azide to provide an alcoholic functionalized mixture of 4- and 5-substituted regioisomers of 1,2,3-triazole moieties. The mixture may be converted to a wide variety of useful functionalized mixtures of 4- and 5-vinyl substituted regioisomers of 1,2,3-triazole moieties, which in turn can be converted to a wide variety of useful polymers. The novel alcoholic functionalized mixtures of 4- and 5-substituted regioisomers can be separated by chromatography to provide the purified 4- and 5-alcoholic functionalized substituted 1,2,3-triazole moieties. The novel mixtures of 4- and 5-vinyl substituted regioisomers can also be separated by chromatography to provide the purified 4- and 5-vinyl substituted 1,2,3-triazole moieties. The novel compounds of the invention can be employed in a wide variety of compositions.

Description of Related Art

The ligation of azides and alkynes using a 1,3-dipolar cycloaddition reaction (azide/alkyne chemistry) has been described in United States patent application 2005/0222427 and in EP patent 1507769. The reaction involves ligation of azides and alkynes in solution using a copper (I) salt catalyst [Cu(I)], or a copper (II) salt catalyst [Cu(II)] in the presence of a reducing agent, such as sodium ascorbate, to provide triazole polymer moieties under ambient conditions ("click reaction"), see H. C. Kolb, M. G. Finn and K. B. Sharpless, *Angew. Chem. Int. Ed.* 2001, 40, 2004-2021. The advantage of the copper catalyzed method over the uncatalyzed method is said to be rate acceleration and exclusive 1,4-regio selectivity. These references also describe azide/alkyne ligation chemistry for the preparation of triazole polymer moieties as metal adhesives using Cu(1) catalysts, prepared by reducing Cu(II) or by oxidizing copper metal to Cu(I) in situ, see D. D. Diaz, S. Punna, P. Holzer, A. K. Mcpherson, K. B. Sharpless, V. V. Fokin, M. G. Finn, *J. Polym. Sci: Part A: Polym. Chem.* 2004, 42, 4392-4403. References that describe the preparation of vinyl-1,2,3-triazole moieties include G. Wouters, et al., *Makromol. Chem.* 183 1861-1868 (1982); Raymond J. Thibault, et al., *J. Am. Chem. Soc.* 2006, 128, 12084-120585; and Kenichi Takizawa, et al., *J. of Polym. Sci.: Part A: Polym. Chem.*, Vol. 46, 2897-2912 (2008).

The copper catalyzed azide/alkyne chemistry requires relatively mild reaction conditions that are not sensitive to air or moisture in contrast to the conditions used in radical polymerizations that are often inhibited by oxygen, leading to incomplete polymerization and reduced yield. Nevertheless, the copper catalyzed azide/alkyne chemistry reactions require the disposal of the catalyst and/or solvent, which adds steps to the synthetic method. It would advantageous to have a method that did not require removal of a catalyst or organic solvent.

SUMMARY OF THE INVENTION

The present invention provides a wide variety of novel alcoholic functionalized 4- and 5-substituted regioisomers of 1,2,3-triazole moieties, which may be converted to useful functionalized 4- and 5-vinyl substituted regioisomers of 1,2,3-triazole moieties. The functionalized 4- and 5-vinyl substituted regioisomers of 1,2,3-triazole moieties may be converted to a wide variety of useful polymers. The novel compounds of the invention can be employed in a wide variety of compositions, such as adhesive, coating, encapsulation, personal care, oilfield, membrane, agricultural, and cleaning compositions.

In one embodiment, the present invention provides an alcoholic mixture of 4- and 5-substituted regioisomers of 1,2,3-triazole moieties. Preferably, the mixture is represented by the structure:

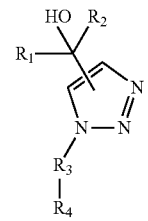

wherein $R_1$, $R_2$, and $R_3$ are independently selected from the group consisting of hydrogen, functionalized and unfunctionalized alkyl, cycloalkyl, alkenyl, and aryl groups, wherein any of the before mentioned groups may be with or without heteroatoms; and $R_4$ is selected from the group consisting of a direct bond, carboxylic acids, esters, amides, anhydrides, aldehydes, ketones, ethers, amines, alcohols, and thiols; with the proviso that when $R_3$ is hydrogen, $R_4$ is a direct bond.

The mixture may also be represented by the structure:

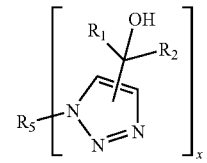

wherein $R_1$ and $R_2$ are as defined above and $R_5$ is selected from the group consisting of functionalized and unfunctionalized alkyl, cycloalkyl, alkenyl, and aryl groups, wherein any of the before mentioned groups may be with or without heteroatoms; and x is an integer ranging from 1 to about 500.

In another embodiment, the present invention provides an 4-alcoholic substituted 1,2,3-triazole moiety represented by the structure:

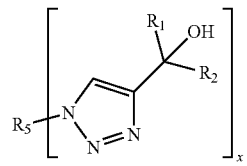

wherein $R_1$, $R_2$, $R_5$ are as defined above and x is an integer ranging from 2 to about 500.

In another embodiment, the present invention provides an 5-alcoholic substituted 1,2,3-triazole moiety represented by the structure:

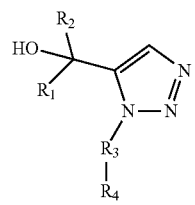

wherein $R_1$, $R_2$, $R_3$, and $R_4$ are as defined above.

The 5-alcoholic substituted 1,2,3-triazole moiety may also be represented by the structure:

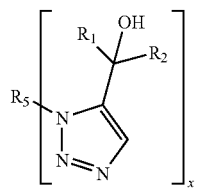

wherein $R_1$, $R_2$, $R_5$ are as defined above and x is an integer ranging from 1 to about 500.

In another embodiment, the present invention provides a mixture of 4- and 5-vinyl substituted regioisomers of 1,2,3-triazole moieties. Preferably, the mixture is represented by the structure:

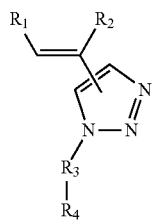

wherein $R_1$, $R_2$, $R_3$, and $R_4$ are as defined above.

The mixture may also be represented by the structure:

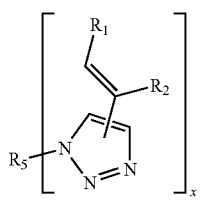

wherein $R_1$, $R_2$, $R_5$ are as defined above and x is an integer ranging from 1 to about 500.

In another embodiment, the present invention provides a 4-vinyl substituted 1,2,3-triazole moiety represented by the structure:

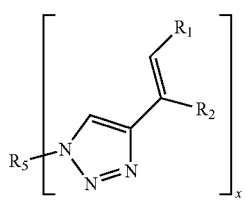

wherein $R_1$, $R_2$, $R_5$ are as defined above and x is an integer ranging from 2 to about 500.

In another embodiment, the present invention provides a 5-vinyl substituted 1,2,3-triazole moiety represented by the structure:

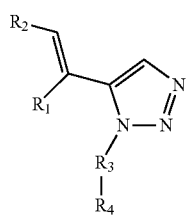

wherein $R_1$, $R_2$, $R_3$, and $R_4$ are as defined above.

The 5-vinyl substituted 1,2,3-triazole moiety may also be represented by the structure:

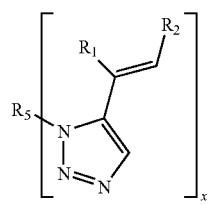

wherein $R_1$, $R_2$, $R_5$ are as defined above and x is an integer ranging from 1 to about 500.

In another embodiment, the present invention provides a homopolymer of a mixture of 4- and 5-vinyl substituted regioisomers of 1,2,3-triazole moieties. Preferably, the homopolymer is represented by the structure:

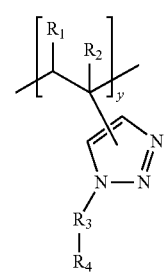

wherein $R_1$, $R_2$, $R_3$, $R_4$ are as defined above and y is an integer ranging from 2 to about 10,000.

In another embodiment, the present invention provides a homopolymer of a 5-vinyl substituted 1,2,3-triazole moiety represented by the structure:

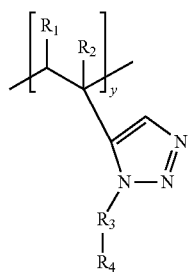

wherein $R_1$, $R_2$, $R_3$, $R_4$ are as defined above and y is an integer ranging from 2 to about 10,000.

In another embodiment, the present invention provides a non-homopolymer of a mixture of 4- and 5-vinyl substituted regioisomers of 1,2,3-triazole moieties with a different polymerizable reactant moiety, wherein the non-homopolymer is a random, blocked, or alternating polymer. Preferably, the non-homopolymer is represented by the structure:

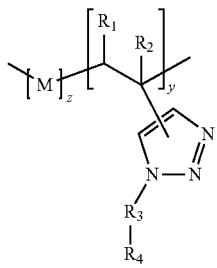

wherein M is based upon a different polymerizable reactant moiety, $R_1$, $R_2$, $R_3$, $R_4$ are as defined above and y and z are integers independently ranging from about 2 to about 10,000, wherein the non-homopolymer is a random, blocked, or alternating polymer.

Preferably, M is based upon a different polymerizable reactant moiety selected from the group consisting of anhydrides, vinyl pyrrolidones, vinyl caprolactams, acrylates, styrenes, malcimides, maleates, fumarates, cinnamyls, vinyl imidazoles, vinyl pyridines, vinyl acetates, acrylamides, vinyl sulfones, vinyl carbonates, vinyl silanes, vinyl acrylamides, allyl alcohols, vinyl ethers, and mixtures thereof.

In another embodiment, the present invention provides a non-homopolymer of a 4-vinyl substituted 1,2,3-triazole moiety with a different polymerizable reactant moiety, wherein the non-homopolymer is a random, blocked, or alternating polymer, wherein the non-homopolymer is represented by the structure:

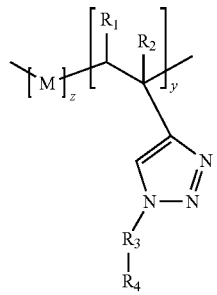

wherein M is based upon a different polymerizable reactant moiety, $R_1$, $R_2$, $R_3$, and $R_4$ are as defined above and y and z are integers independently ranging from about 2 to about 10,000, wherein the non-homopolymer is a random, blocked, or alternating polymer.

In another embodiment, the present invention provides a non-homopolymer of a 5-vinyl substituted 1,2,3-triazole moiety with a different polymerizable reactant moiety, wherein the non-homopolymer is a random, blocked, or alternating polymer, wherein the non-homopolymer is represented by the structure:

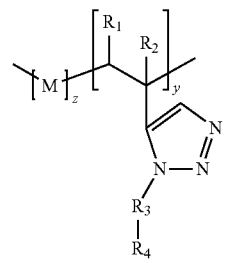

wherein M is based upon a different polymerizable reactant moiety, wherein $R_1$, $R_2$, $R_3$, $R_4$ are as defined above and y and z are integers independently ranging from about 2 to about 10,000, wherein the non-homopolymer is a random, blocked, or alternating polymer.

DETAILED DESCRIPTION OF THE INVENTION

The present invention provides a new vinyl monomer family, which combines the desirable features of thermal and chemical stability while providing functional versatility. Vinyl triazole monomers are a significant advance beyond classic vinyl monomers derived from styrenic, acrylate, or α-olefin-based monomer systems. The invention demonstrates the utility of cycloaddition of azides and alkynes resulting in unique vinylic triazole monomers. This utility is supported by the benign (environmentally friendly) character of cycloaddition reaction conditions, functional group tolerance, quantitative yields and relevance to a broad range of applications. These applications encompass adhesive, coating, encapsulation, personal care, oilfield, membrane, agricultural, and cleaning compositions. As found in styrenics, vinyl pyridines, and acrylates, vinyl-1,2,3-triazoles possess attractive features including stability, aromaticity, polarity, and versatility with substitutions at N-1. This new vinyl monomer family may be employed to yield novel vinyl triazole homopolymers and non-homopolymers with, for example, anhydrides, vinyl pyrrolidones, vinyl caprolactams, acrylates, styrenes, maleimides, maleates, fumarates, cinnamyls, vinyl imidazoles, vinyl pyridines, vinyl acetates, acrylamides, vinyl sulfones, vinyl carbonates, vinyl silanes, vinyl acrylamides, allyl alcohols, vinyl ethers, itaconic anhydrides, and citraconic anhydrides.

As used herein, the following terms have the meanings set out below.

The term "alkyne moiety" refers to an alkyne group, which may be attached to an unsubstituted or substituted alkyl, cycloalkyl, alkenyl, and aryl groups, wherein any of the before mentioned groups may be present with or without heteroatoms. The alkyl and alkenyl groups may be branched or unbranched (straight-chain). Preferably, the alkyl and alkenyl groups are $C_1$-$C_{60}$, more preferably $C_1$-$C_{36}$, and most preferably $C_1$-$C_{18}$ groups. Cycloalkyls (closed rings) include cyclopentane, cyclohexane, cycloheptane, and the like. Aryl groups include benzenes, naphthalenes (2 rings), and anthracenes (3 rings), and the like.

The symbol of a "bond to the middle of a vinyl group" means that the bond can be attached to either side of the vinyl group and generally means that the structure is referring to a mixture of isomers. For example, in the structure below:

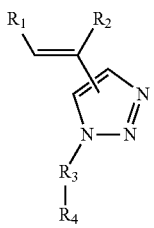

the vinyl group containing $R_1$ and $R_2$ can be attached to either the 4 or the 5 position of the 1,2,3-triazole moiety.

The term "direct bond' means that the group can be nothing.

The term "free radical addition polymerization initiator" refers to a compound used in a catalytic amount to initiate a free radical addition polymerization. The choice of initiator depends mainly upon its solubility and its decomposition temperature.

The term "functionalized mixture of 4- and 5-vinyl substituted regioisomers of 1,2,3-triazole moieties" refers to mixtures of 1,2,3-triazole moieties substituted with a vinyl group at the 4 and 5 position on the 1,2,3-triazole. Some non-limiting examples of structures of functionalized mixtures of 4- and 5-vinyl substituted regioisomers of 1,2,3-triazole moieties include:

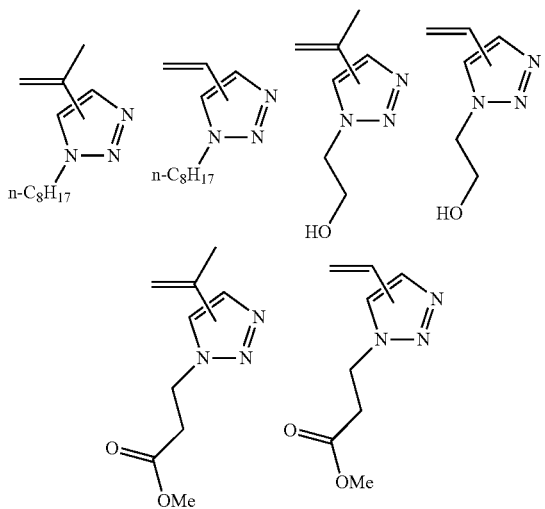

The term "halogen" refers to chloro, bromo, iodo and fluoro, and is preferably bromo or chloro.

The term "heteroatom" refers to atoms such as oxygen, nitrogen, sulfur, and phosphorous.

The term "homopolymer" refers to a polymer formed from a single monomer.

The term "inert solvent" refers to a solvent that does not interfere chemically with the reaction.

The term "leaving group" refers to any group that can be displaced by an azide ion. Nonlimiting examples include halogens, silyl groups, tosyl groups, and mesyl groups.

The term "ligation" refers to an act of uniting or connecting two or more starting materials or reactants.

The term "non-homopolymer" refers to a polymer formed from two or more monomers and includes essentially all polymers that are not homopolymers. Nonlimiting examples of non-homopolymers include copolymers, terpolymers, tetramers, and the like, wherein the non-homopolymer is a random, blocked, or alternating polymer.

The terms "mixture of 4- and 5-vinyl substituted regioisomers of 1,2,3-triazole moieties", "4-vinyl substituted regioisomers of 1,2,3-triazole moieties", and "5-vinyl substituted regioisomers of 1,2,3-triazole moieties" refer to vinyl substituted 1,2,3-triazole moieties having, for example, the structure shown below for the mixture of 4- and 5-vinyl substituted regioisomers:

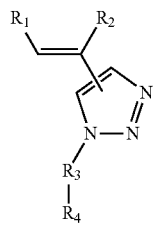

The configuration of the $R_1$ and $R_2$ groups on the vinyl bond is not meant to suggest any particular type of stereoisomerism about the double bond. Traditionally, double bond stereochemistry was described as either cis (on this side) or trans (across), in reference to the relative position of substituents on either side of the double bond. IUPAC adopted a more rigorous system wherein the substituents at each end of the double bond are assigned priority based on their atomic number. If the high priority substituents are on the same side of the bond, it is assigned Z (zusammen, together). If they are on opposite sides, it is E (entgegen, opposite). The structures of the vinyl substituted regioisomers of 1,2,3-triazole moieties referred to in the present invention can either be in the E or Z configuration, or mixtures thereof.

The term "monomer" refers to the repeat units comprising a polymer. A monomer is a small molecule that chemically bonds to other monomers to form a polymer.

The term "organic moiety" refers to an unsubstituted or substituted alkyl, cycloalkyl, alkenyl, and aryl groups, wherein any of the before mentioned groups may be present with or without heteroatoms. The alkyl and alkenyl groups may be branched or unbranched (straight-chain). Preferably, the alkyl and alkenyl groups are $C_1$-$C_{60}$, more preferably $C_1$-$C_{36}$, and most preferably $C_1$-$C_{18}$ groups. Cycloalkyls (closed rings) include cyclopentane, cyclohexane, cycloheptane, and the like. Aryl groups include benzenes, naphthalenes (2 rings), and anthracenes (3 rings), and the like.

The term "personal care composition" refers to such illustrative non-limiting compositions as skin, sun, oil, hair, cosmetic, and preservative compositions, including those to alter the color and appearance of the skin. Potential personal care compositions include, but are not limited to, polymers for increased flexibility in styling, durable styling, increased humidity resistance for hair, skin, and color cosmetics, sun care water-proof/resistance, wear-resistance, and thermal protecting/enhancing compositions.

The term "polymer" refers to a large molecule (macromolecule) composed of repeating structural units (monomers) connected by covalent chemical bonds.

The term "x" refers to an integer commonly used in polymers and denotes the number of repeating units of each monomer. In general, x in the present invention is about 1 to about 500, preferably from about 2 to about 500, and more preferably from about 1 or 2 to about 400.

The terms "y" and "z" refer to integers commonly used in polymers and denote the number of repeating units of each monomer. In general, y and z in the present invention are independently from about 2 to about 10,000, preferably from about 100 to about 10,000, and more preferably from about 1,000 to about 10,000.

As set out above, the present invention provides a wide variety of novel alcoholic functionalized 4- and 5-substituted regioisomers of 1,2,3-triazole moieties, which may be converted to useful functionalized 4- and 5-vinyl substituted regioisomers of 1,2,3-triazole moieties. The functionalized 4- and 5-vinyl substituted regioisomers of 1,2,3-triazole moieties may be converted to a wide variety of useful polymers. The novel compounds of the invention can be employed in a wide variety of compositions, such as adhesive, coating, encapsulation, personal care, oilfield, membrane, agricultural, and cleaning compositions.

In one embodiment, the present invention provides an alcoholic mixture of 4- and 5-substituted regioisomers of 1,2,3-triazole moieties. Preferably, the mixture is represented by the structure:

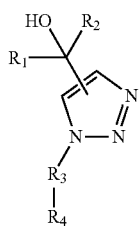

wherein $R_1$, $R_2$, and $R_3$ are independently selected from the group consisting of hydrogen, functionalized and unfunctionalized alkyl, cycloalkyl, alkenyl, and aryl groups, wherein any of the before mentioned groups may be with or without heteroatoms; and $R_4$ is selected from the group consisting of a direct bond, carboxylic acids, esters, amides, anhydrides, aldehydes, ketones, ethers, amines, alcohols, and thiols; with the proviso that when $R_3$ is hydrogen, $R_4$ is a direct bond.

The mixture may also be represented by the structure:

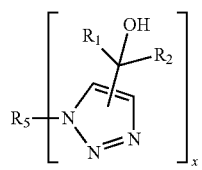

wherein $R_1$ and $R_2$ are as defined above and $R_5$ is selected from the group consisting of functionalized and unfunctionalized alkyl, cycloalkyl, alkenyl, and aryl groups, wherein any of the before mentioned groups may be with or without heteroatoms; and x is an integer ranging from 1 to about 500.

In another embodiment, the present invention provides an 4-alcoholic substituted 1,2,3-triazole moiety represented by the structure:

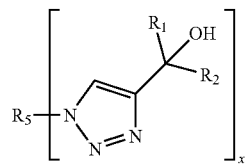

wherein $R_1$, $R_2$, $R_5$ are as defined above and x is an integer ranging from 2 to about 500.

In another embodiment, the present invention provides an 5-alcoholic substituted 1,2,3-triazole moiety represented by the structure:

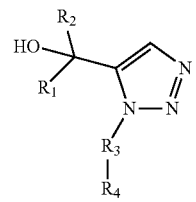

wherein $R_1$, $R_2$, $R_3$, and $R_4$ are as defined above.

The 5-alcoholic substituted 1,2,3-triazole moiety may also be represented by the structure:

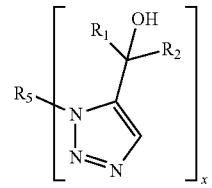

wherein $R_1$, $R_2$, $R_5$ are as defined above and x is an integer ranging from 1 to about 500.

In another embodiment, the present invention provides a mixture of 4- and 5-vinyl substituted regioisomers of 1,2,3-triazole moieties. Preferably, the mixture is represented by the structure:

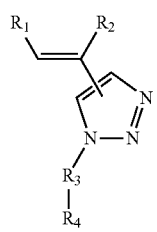

wherein $R_1$, $R_2$, $R_3$, and $R_4$ are as defined above.

The mixture may also be represented by the structure:

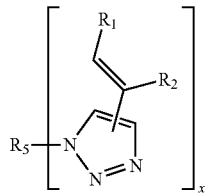

wherein $R_1$, $R_2$, $R_5$ are as defined above and x is an integer ranging from 1 to about 500.

In another embodiment, the present invention provides a 4-vinyl substituted 1,2,3-triazole moiety represented by the structure:

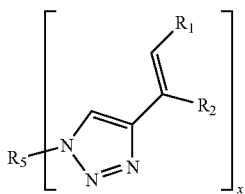

wherein $R_1$, $R_2$, $R_5$ are as defined above and x is an integer ranging from 2 to about 500.

In another embodiment, the present invention provides a 5-vinyl substituted 1,2,3-triazole moiety represented by the structure:

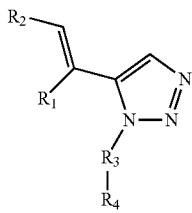

wherein $R_1$, $R_2$, $R_3$, and $R_4$ are as defined above.

The 5-vinyl substituted 1,2,3-triazole moiety may also be represented by the structure:

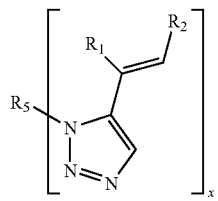

wherein $R_1$, $R_2$, $R_5$ are as defined above and x is an integer ranging from to about 500.

In another embodiment, the present invention provides a homopolymer of a mixture of 4- and 5-vinyl substituted regioisomers of 1,2,3-triazole moieties. Preferably, the homopolymer is represented by the structure:

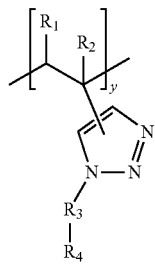

wherein $R_1$, $R_2$, $R_3$, $R_4$ are as defined above and y is an integer ranging from 2 to about 10,000.

In another embodiment, the present invention provides a homopolymer of a 5-vinyl substituted 1,2,3-triazole moiety represented by the structure:

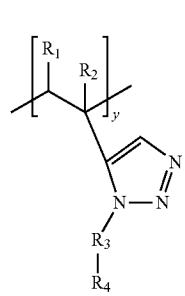

wherein $R_1$, $R_2$, $R_3$, $R_4$ are as defined above and y is an integer ranging from 2 to about 10,000.

In another embodiment, the present invention provides a non-homopolymer of a mixture of 4- and 5-vinyl substituted regioisomers of 1,2,3-triazole moieties with a different polymerizable reactant moiety, wherein the non-homopolymer is a random, blocked, or alternating polymer. Preferably, the non-homopolymer is represented by the structure:

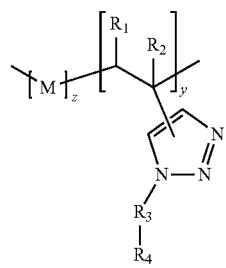

wherein M is based upon a different polymerizable reactant moiety, $R_1$, $R_2$, $R_3$, $R_4$ are as defined above and y and z are integers independently ranging from about 2 to about 10,000, wherein the non-homopolymer is a random, blocked, or alternating polymer.

In another embodiment, the present invention provides a non-homopolymer of a 4-vinyl substituted 1,2,3-triazole moiety with a different polymerizable reactant moiety, wherein the non-homopolymer is a random, blocked, or alternating polymer, wherein the non-homopolymer is represented by the structure:

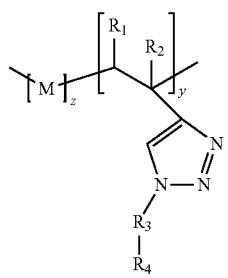

wherein M is based upon a different polymerizable reactant moiety, $R_1$, $R_2$, $R_3$, and $R_4$ are as defined above and y and z are integers independently ranging from about 2 to about 10,000, wherein the non-homopolymer is a random, blocked, or alternating polymer.

In another embodiment, the present invention provides a non-homopolymer of a 5-vinyl substituted 1,2,3-triazole moiety with a different polymerizable reactant moiety, wherein the non-homopolymer is a random, blocked, or alternating polymer, wherein the non-homopolymer is represented by the structure:

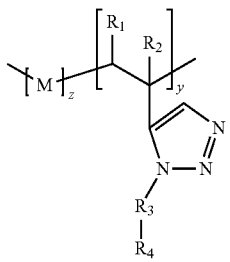

wherein M is based upon a different polymerizable reactant moiety, wherein $R_1$, $R_2$, $R_3$, and $R_4$ are as defined above and y and z are integers independently ranging from about 2 to about 10,000, wherein the non-homopolymer is a random, blocked, or alternating polymer.

The synthesis of the functionalized mixtures of 4- and 5-vinyl substituted regioisomers of 1,2,3-triazole moieties is a three-step method. Multiple chemical transformations occur in solution leading to the desired functionalized mixtures of 4- and 5-vinyl substituted regioisomers of 1,2,3-triazole moieties. In the first step, conditions for preparation of the triazole intermediate are environmentally friendly. For example, the reaction of an alkyne moiety with a terminal alcoholic functionality, such as 2-methylbut-3-yn-2-ol, sodium azide and an organic moiety with a terminal leaving group, such as an alkyl or aryl halide, is carried out in an aqueous medium without catalyst(s). Following in-situ generation of the azide derivative (displacement of the leaving group by the azide ion), a triazole "nucleus" is formed (1,3 cycloaddition of the azide to the alkyne) and isolated as an alcoholic functionalized mixture of 4- and 5-substituted regioisomers of 1,2,3-triazole moieties. Water is then removed from the alcoholic 1,2,3-triazole moieties and, in the third step, the triazole intermediates can then be readily dehydrated with, for example, phosphorus oxychloride in the presence of pyridine, triethyl amine, or other bases, or alternatively by simply heating the mixture. This reaction delivers a high yield of the desired N-1 substituted 4- and 5-vinyl substituted regioisomers of 1,2,3-triazole moieties. An attractive feature of this synthetic approach is the versatility afforded by the wide variety of alkyl/aryl halide starting reagents available. Thus, a wide variety of functionalized mixture of 4- and 5-vinyl substituted regioisomers of 1,2,3-triazole moieties with various N-1 substituents can be readily obtained. The functionalized mixtures of 4- and 5-vinyl substituted regioisomers of 1,2,3-triazole moieties can be converted to a wide variety of useful polymers. The novel alcoholic functionalized mixtures of 4- and 5-substituted regioisomers can be separated by chromatography to provide the purified 4- and 5-alcoholic functionalized substituted 1,2,3-triazole moieties. The novel mixtures of 4- and 5-vinyl substituted regioisomers can also be separated by chromatography to provide the purified 4- and 5-vinyl substituted 1,2,3-triazole moieties. The novel compounds of the invention can be employed in a wide variety of compositions.

The alkyne moiety may be an unsubstituted or substituted alkyl, cycloalkyl, alkenyl, and aryl groups, wherein any of the before mentioned groups may be present with or without heteroatoms. Preferably, the alkyne moiety is selected from the group consisting of 2-methyl-3-butyn-2-ol, propargyl alcohol, but-3-yn-2-ol, 3,6-dimethyl-4-octyne-3,6-diol, 1-phenyl-1-hexyn-3-ol, 1-phenyl-4-methyl-1-pentyn-3-ol, 7-methoxy-3,7-dimethyl-oct-1-yn-3-ol, 3,8 dihydroxy-3,8-dimethyl-4,6-decadiyne, 1-trimethylsilanylethynyl-cyclohexanol, 1-phenyl-3-pentyn-2-ol, 4-bromo-2-methyl-3-butyn-2-ol, 2-(2-fluorophenyl)-3-butyn-2-ol, 2-(4-fluorophenyl)-3-butyn-2-ol, 2-(3-fluorophenyl)-3-butyn-2-ol, 2,7-dimethyl-3,5-octadiyne-2,7-diol, 2,6-dimethyl-oct-2-en-7-yne-1,6-diol, (S)-(−)-3-butyn-2-ol, (R)-(+)-3-butyn-2-ol, and 3-pentyn-2-ol. More preferably, the alkyne moiety is 2-methyl-3-butyn-2-ol.

The organic moiety with a terminal leaving group may be an unsubstituted or substituted alkyl, cycloalkyl, alkenyl, and aryl groups, wherein any of the before mentioned groups may be present with or without heteroatoms. Preferably, the organic moiety is selected from the group consisting of 1-bromooctane, methyl-3-bromopropionate, 2-chloroethanol, 2-(2-chloroethoxy)ethanol, (dimethylamino)ethylchloride, 3-chloro-1-propene, 2-chloroacetamide, acetyl chloride, 1-chloropropane, chloromethyl octyl ether, bromoethane, bromoacetonitrile, 3-bromo-1-pentene, 2-bromopropane, 3-bromofuran, and 2-bromoimidazole. More preferably, the organic moiety is selected from the group consisting of 1-bromooctane, methyl-3-bromopropionate, 2-chloroethanol, 2-(2-chloroethoxy)ethanol, and (dimethylamino)ethylchloride.

The terminal leaving group in the organic moiety may be selected from the group consisting of halogens, silyl groups, tosyl groups, and mesyl groups. Preferably, the leaving group is a halogen. More preferably, the leaving groups are chloro or bromo.

The dehydrating agent may be selected from the group consisting of $POCl_3$, acetic acid, nitric acid, sulfuric acid, and molecular sieves.

The alcoholic mixture of 4- and 5-substituted regioisomers of 1,2,3-triazole moieties is preferably represented by the structure:

15

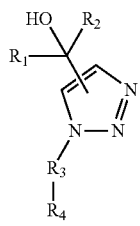

wherein $R_1$, $R_2$, $R_3$, and $R_4$ are as defined above.

Preferably, the alcoholic functionalized mixture of 4- and 5-substituted regioisomers of 1,2,3-triazole moieties may be selected from the group consisting of:

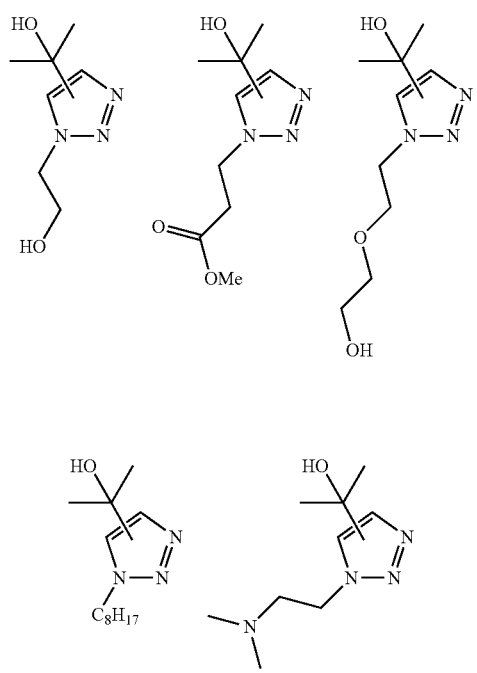

More preferably, the alcoholic functionalized mixture of 4- and 5-substituted regioisomers of 1,2,3-triazole moieties is:

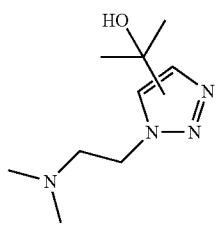

The functionalized mixture of 4- and 5-vinyl substituted regioisomers of 1,2,3-triazole moieties is preferably represented by the structure:

16

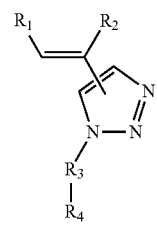

wherein $R_1$, $R_2$, $R_3$, and $R_4$ are as defined above.

Preferably, the functionalized mixture of 4- and 5-vinyl substituted regioisomers of 1,2,3-triazole moieties may be selected from the group consisting of:

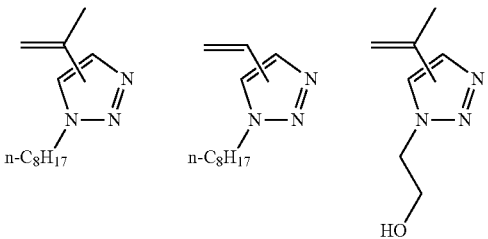

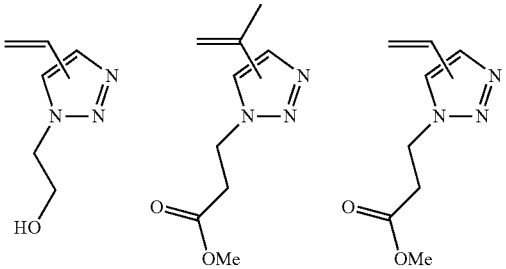

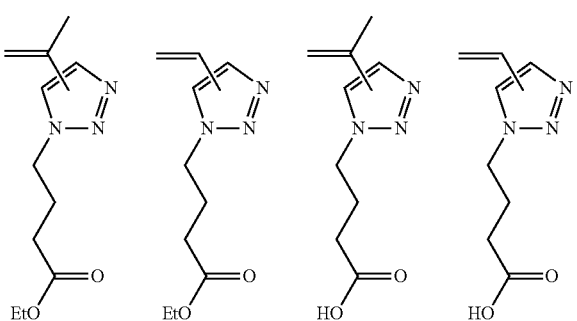

-continued

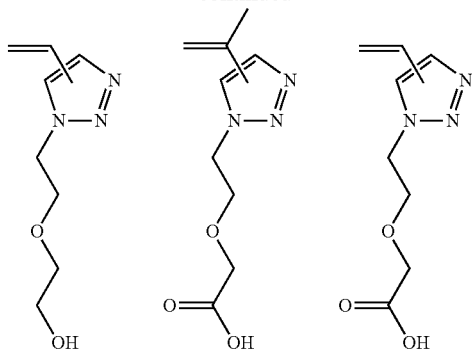

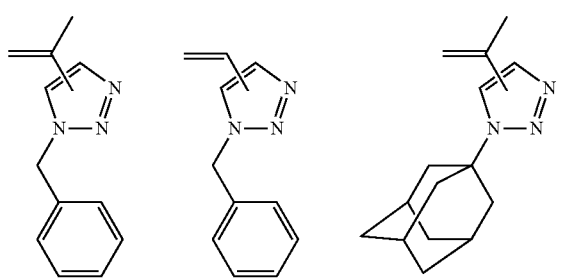

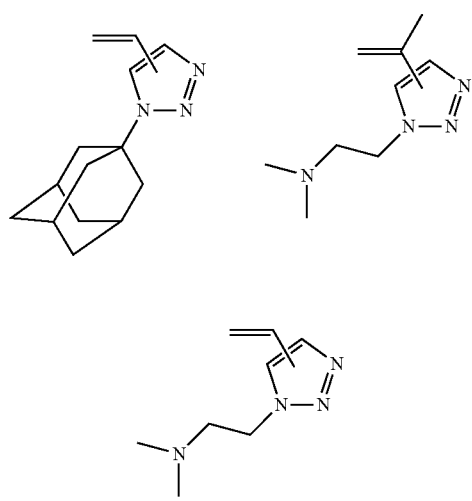

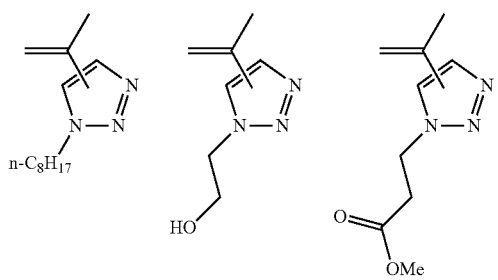

More preferably, the functionalized mixture of 4- and 5-vinyl substituted regioisomers of 1,2,3-triazole moieties may be selected from the group consisting of:

-continued

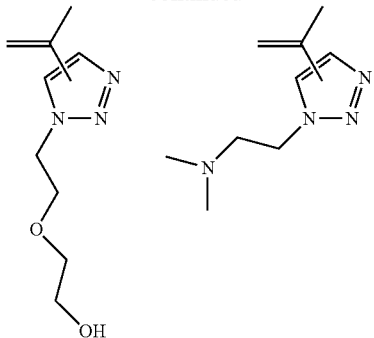

Most preferably, the functionalized mixture of 4- and 5-vinyl substituted regioisomers of 1,2,3-triazole moieties is:

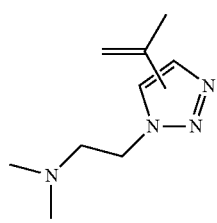

In another embodiment, the present invention provides a homopolymer of a mixture of 4- and 5-vinyl substituted regioisomers of 1,2,3-triazole moieties. Preferably, the homopolymer is represented by the structure:

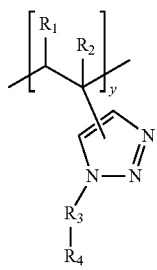

wherein $R_1$, $R_2$, $R_3$, $R_4$ are as defined above and y is an integer ranging from 2 to about 10,000.

In another embodiment, the present invention provides a homopolymer of a 5-vinyl substituted 1,2,3-triazole moiety represented by the structure:

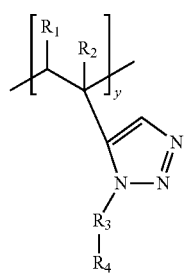

wherein $R_1$, $R_2$, $R_3$, $R_4$ are as defined above and y is an integer ranging from 2 to about 10,000.

The functionalized mixture of 4- and 5-vinyl substituted regioisomers of 1,2,3-triazole moieties may be polymerized with a different polymerizable reactant moiety to form a non-homopolymer. Preferably, the different polymerizable reactant moiety may be selected from the group consisting of anhydrides, vinyl pyrrolidones, vinyl caprolactams, acrylates, styrenes, maleimides, maleates, fumarates, cinnamyls, vinyl imidazoles, vinyl pyridines, vinyl acetates, acrylamides, vinyl sulfones, vinyl carbonates, vinyl silanes, vinyl acrylamides, allyl alcohols, vinyl ethers, and mixtures thereof.

Illustrative, non-limiting examples of anhydrides include maleic anhydride, phthalic anhydride, lauric anhydride, pyromellitic anhydride, trimellitic anhydride, hexahydrophthalic anhydride; hexahydropyromellitic anhydride, hexahydrotrimellitic anhydride, itaconic anhydrides, citraconic anhydrides, and mixtures thereof.

More preferably, the different polymerizable reactant moiety may be selected from the group consisting of:

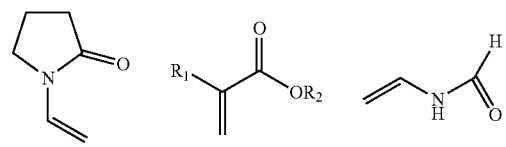
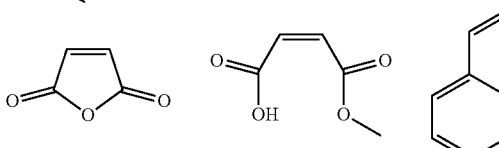
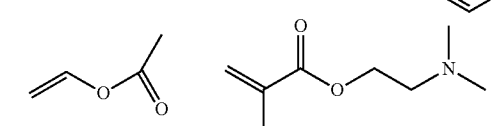
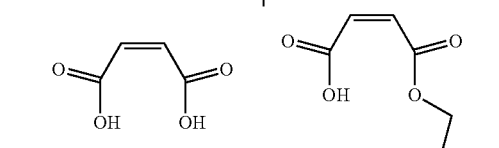

wherein $R_1$ and $R_2$ are as defined above.

Most preferably, the different polymerizable reactant moiety is selected from the group consisting of:

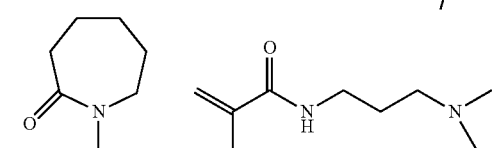
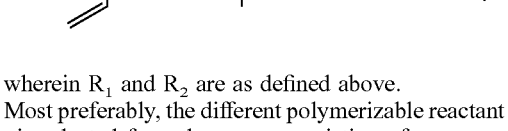
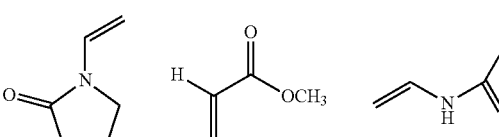
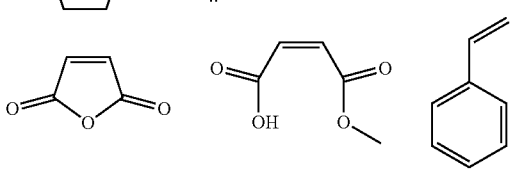

The non-homopolymer may be selected from the group consisting of:

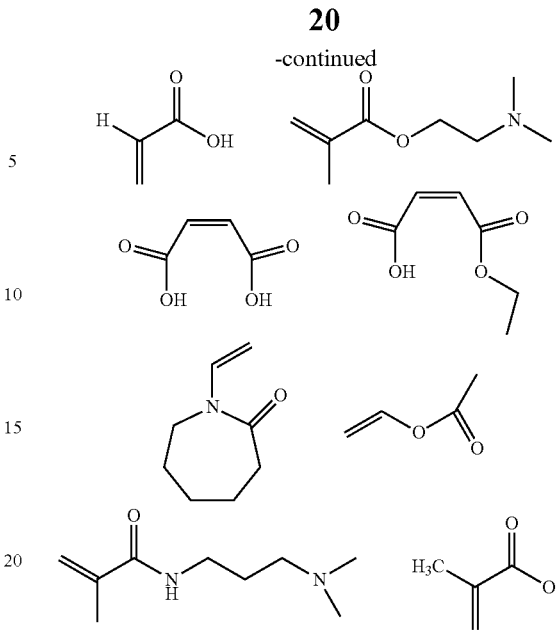
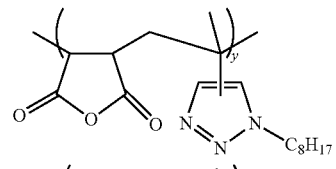
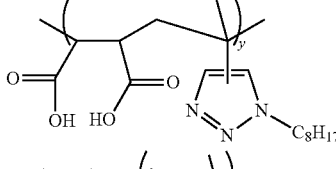
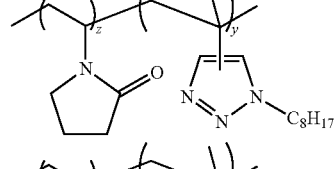
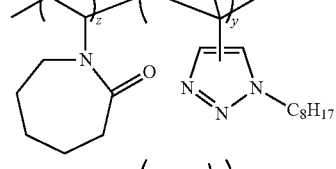
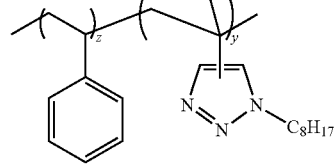
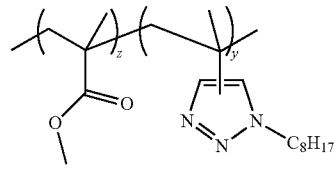

-continued

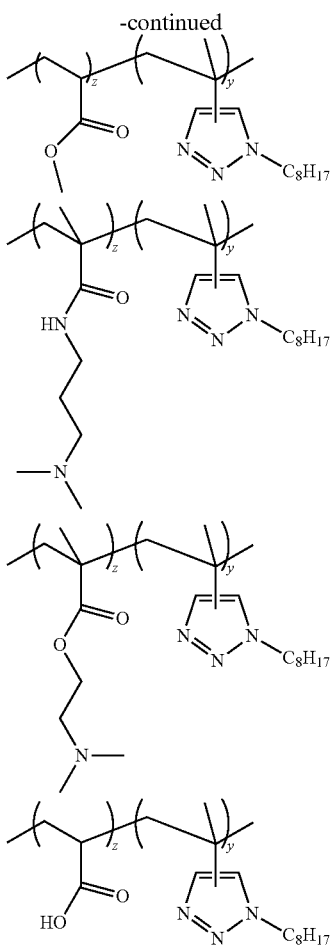

wherein y and z are integers independently ranging from about 2 to about 10,000.

The present invention also provides a two-part composition comprising a first part and a second part wherein (1) the first part comprises a functionalized mixture of 4- and 5-vinyl substituted regioisomers of 1,2,3-triazole moieties comprising: (a) reacting a first reactant having a functionalized alkyne moiety with a terminal alcoholic functionality and a second reactant having an unsubstituted or substituted organic moiety with a terminal leaving group with sodium azide in water, in the absence of a catalyst or an organic solvent, to provide an alcoholic functionalized mixture of 4- and 5-substituted regioisomers of 1,2,3-triazole moieties; (b) removing the water from the mixture in step (a); and (c) dehydrating the alcoholic functionalized mixture of 4- and 5-substituted regioisomers of the 1,2,3-triazole moieties from step (b) with a dehydrating agent or by heating the mixture to provide a functionalized mixture of 4- and 5-vinyl substituted regioisomers of 1,2,3-triazole moieties; and (2) the second part comprises a polymerizable reactant moiety, which can be the same as the functionalized mixture of 4- and 5-vinyl substituted regioisomers of 1,2,3-triazole moieties of the first part or a different polymerizable reactant moiety; wherein the first reactant and the second reactant of the two-part composition are admixed under polymeric conditions to form a polymeric moiety.

The different polymerizable reactant moiety in the second part may be selected from the group consisting of anhydrides, vinyl pyrrolidones, vinyl caprolactams, acrylates, styrenes, maleimides, maleates, fumarates, cinnamyls, vinyl imidazoles, vinyl pyridines, vinyl acetates, acrylamides, vinyl sulfones, vinyl carbonates, vinyl silanes, vinyl acrylamides, allyl alcohols, vinyl ethers, and mixtures thereof. Suitable examples of these different polymerizable reactant moieties are as described above.

The present invention also provides an adhesive, coating, encapsulation, personal care, oilfield, membrane, agricultural, and cleaning compositions comprising the above-described homopolymer. The present invention also provides an adhesive, coating, encapsulation, personal care, oilfield, membrane, agricultural, and cleaning compositions comprising the above-described non-homopolymer. The present invention also provides an adhesive, coating, encapsulation, personal care, oilfield, membrane, agricultural, and cleaning compositions comprising the above-described two-part composition. These polymers may be used in any industrial field. It is of particular use for electronic, electrical, opto-electronic, and photo-electronic applications. Such applications include die attach adhesives, underfill encapsulants, antennae for radio-frequency identification (RFID), via holes, film adhesives, conductive inks, circuit board fabrication, other laminate end uses, and other uses with printable electronics.

Because the method of the present invention does not employ a catalyst, the method provides functionalized mixtures of 4- and 5-vinyl substituted regioisomers of 1,2,3-triazole moieties. Catalyzed methods would provide mainly the 4-vinyl substituted regioisomer. The mixtures of 4- and 5-vinyl substituted regioisomers may be separated by conventional chromatographic methods to provide the purified 4-vinyl substituted regioisomers and the 5-vinyl substituted regioisomers. The 5-vinyl substituted 1,2,3-triazole moiety cannot be prepared by a catalyzed method. The purified 4-vinyl substituted regioisomers and the 5-vinyl substituted regioisomers may then be employed to prepare 4-vinyl substituted and 5-vinyl substituted homopolymers and non-homopolymers Chromatography is the collective team for a group of laboratory techniques for the separation of mixtures. The techniques involve passing a mixture dissolved in a mobile phase through a stationary phase, which separates the analyte to be measured from other molecules in the mixture and allows it to be isolated. Preparative chromatography, the preferred technique to be employed in this invention, separates the components of a mixture for further use and is thus a form of purification. The various forms of chromatography are well known to those of skill in the art. The most general technique for separating large amounts of material is column chromatography. Column chromatography is a separation technique in which the stationary bed is within a tube. The particles of the solid stationary phase or the support coated with a liquid stationary phase may fill the whole inside volume of the tube (packed column) or be concentrated on or along the inside tube wall leaving an open, unrestricted path for the mobile phase in the middle part of the tube. Differences in rates of movement through the medium are calculated to different retention times of the sample. Another technique that may be employed is liquid chromatography, which is a separation technique in which the mobile phase is a liquid. Liquid chromatography can be carried out either in a column or a plane. Liquid chromatography that generally utilizes very small packing particles and a relatively high pressure is referred to as high performance liquid chromatography (HPLC). In the HPLC technique, the sample is forced through a column that is packed with irregularly or spherically shaped particles or a porous monolithic layer (stationary phase) by a liquid (mobile phase) at high pressure. HPLC is generally divided into two different sub-classes based on the polarity of the mobile and stationary phases. The technique in which the stationary phase is more polar than the mobile phase is called natural phase liquid chromatography (NPLC) and the opposite is called reversed phase liquid chromatography (RPLC). Reversed-phase chromatography is an elution procedure used in liquid chromatography in which the mobile phase is significantly more polar than the stationary phase. The appropriate method and conditions of chromatography to separate the mixtures of 4- and 5-substituted regioisomers are well known in the art.

As set out above, the availability of various N-1 substituent options allows for the custom manufacturing of polymers with specific physical property properties. For example when the N-1 substituent is n-$C_8H_{17}$, one obtains a hydrophobic functionalized mixture of 4- and 5-vinyl substituted regioisomers of 1,2,3-triazole moieties. On the other hand, when the N-1 substituent is $CH_2CH_2OH$, $CH_2CH_2OCH_2CH_2OH$, or $CH_2CH_2N(CH_3)_2$, one obtains a hydrophilic functionalized mixture of 4- and 5-vinyl substituted regioisomers of 1,2,3-triazole moieties.

Optionally, a free radical addition polymerization initiator may be employed in the polymerization reaction. Non-limiting illustrative examples of free radical addition polymerization initiators include 2,2'-azobis(2-methylpropionitrile) and benzoyl peroxide. A preferred free radical addition polymerization initiator is 2,2'-azobis(2-methylpropionitrile).

Depending on the end application, one or more fillers may be included in the compositions and usually are added for improved rheological properties and stress reduction. Examples of suitable nonconductive fillers include alumina, aluminum hydroxide, silica, fused silica, fumed silica, vermiculite, mica, wollastonite, calcium carbonate, titania, sand, glass, barium sulfate, zirconium, carbon black, organic fillers, and halogenated ethylene polymers, such as, tetrafluoroethylene, trifluoroethylene, vinylidene fluoride, vinyl fluoride, vinylidene chloride, and vinyl chloride. Examples of suitable conductive fillers include carbon black, graphite, gold, silver, copper, platinum, palladium, nickel, aluminum, silicon carbide, boron nitride, diamond, and alumina.

The filler particles may be of any appropriate size ranging from nano size to several mm. The choice of such size for any particular end use is within the expertise of one skilled in the art. The filler may be present in an amount from 10 to 90% by weight of the total composition. More than one filler type may be used in a composition and the fillers may or may not be surface treated. Appropriate filler sizes can be determined by the practitioner, but, in general, will be within the range of 20 nanometers to 100 microns.

Other materials, such as adhesion promoters (e.g. epoxides, silanes), dyes, pigments, and rheology modifiers may be added as desired for the modification of the final properties. Such materials and the amounts needed are within the expertise of those skilled in the art.

The compounds of the present invention can be prepared according to the examples set out below. The examples are presented for purposes of demonstrating, but not limiting, the preparation of the compounds and compositions of this invention.

EXAMPLES

In accordance with the present invention, the following examples are provided to illustrate preferred methods for preparing novel methods for the ligation of azides and alkynes using 1,3-dipolar cycloaddition reactions to provide a functionalized mixture of 4- and 5-vinyl substituted regioisomers of 1,2,3-triazole monomers, which may be converted to a wide variety of useful functionalized mixture of 4- and 5-vinyl substituted regioisomers of 1,2,3-triazole polymers.

Example 1

Synthesis of 2-(1-octyl-1H-1,2,3-triazol-4-yl)propan-2-ol

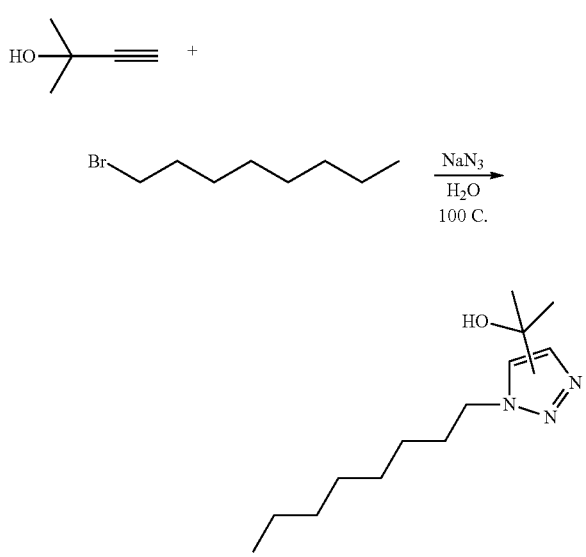

A 2-liter 4-neck round-bottom reaction flask was equipped with a mechanical mixer, reflux condenser, heating mantle, temperature probe and temperature controller. The flask was charged with water (464 grams), sodium azide (100.0 grams, 1.5382 mol), 2-methyl-3-Butyn-2-ol (117.6 grams, 1.3984 mol) and 1-bromooctane (270.1 grams, 1.3984 mol). A continuous mild air purge was applied to sweep the contents of the flask. The set-point of the internal temperature controller was initially set to 95° C. The contents were mixed vigorously at 400 rpms. The reaction was heated to reflux and maintained at a temperature between 92 and 97° C.; the temperature controller set-point was adjusted accordingly. Reaction conversion was monitored via thin-layer chromatography using an ethyl acetate/hexane solvent system of 4/1 by volume, respectively. After 24 hours of being heated at reflux, the reaction was discharged to a 2-liter reparatory funnel to cool. While cooling, the reaction "phased out" to a clear yellow organic layer over a clear and colorless aqueous layer. The organic layer (product solution) was collected and the bottom aqueous layer was discarded. The product solution was diluted with 320 ml of ethyl acetate. Hexane (80 ml) and silica gel (40 grams) were added to the mixture, which was then stirred for 1 hour. The silica gel was removed by filtration leaving a clear yellow product solution. The solvent was then removed via roto-evaporation over about 2 hours at 85-90° C. and ~250 Torr. The product was collected as a clear, yellow low-viscosity oil. The structure of this triazole was confirmed by NMR and LC-MS.

Example 2

Synthesis of 1-octyl-4-(prop-1-en-2-yl)-1H-1,2,3-triazole

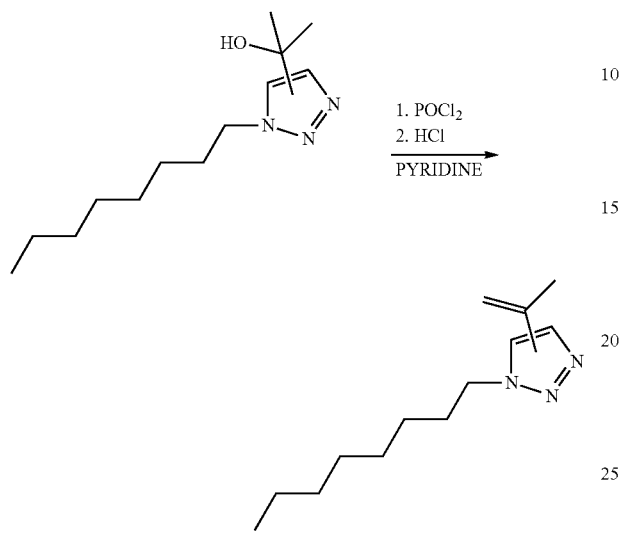

A 3 L 4-neck round bottom reaction flask was equipped with a mechanical stirrer, temperature probe/controller, condenser and ice bath/heating mantle. The flask was charged with 2-(1-octyl-1H-1,2,3-triazol-4-yl)propan-2-ol (100 grams, 0.4184 mol) and pyridine (870.1 grams, 26.3 mol) at room temperature. The clear gold solution was mixed for 5 minutes. A slow-addition funnel charged with $POCl_3$ was mounted on the flask. The flask and contents were chilled to ~0° C. in the ice bath. $POCl_3$ (128.3 grams, 0.8368 mol) was added drop-wise while maintaining a reaction temperature</=5° C. At this scale, the addition lasted ~1.25 hrs and the reaction temperature ranged from about 2 to 5° C. The reaction flask was then fitted with a heating mantle and the contents were mixed and heated to reflux for 3 hours at a reaction temperature~120° C. By the end of 3 hours, the reaction was a clear dark-brown solution. The reaction solution was poured into a 2 L separatory funnel charged with ~500 ml of ice. [Beware of heat generated by the dissolution of HCl, a by-product of the reaction.] Time was allowed for the contents of the separatory funnel to cool and "phase-out". The top dark brown "oil" phase was then isolated. The bottom dark-brown aqueous phase was extracted twice with 200 ml of ethyl acetate per extraction. The oil phase and the extractions were combined, thereby forming the "product solution". The product solution was washed repeatedly with 500 mL of 1M HCl. After each wash, the pH of the wash water was measured. The acid washing step was repeated until the pH of the wash water matched the pH of the 1M HCl solution (~0-1). A pH of 0-1 was achieved by the end of the fourth wash in this example. The acid washes were followed by a final wash using 300 mL of saturated sodium bicarbonate solution. The pH of the final wash was ~9. The product solution was then collected, dried over 10 grams of magnesium sulfate and filtered. Removal of the solvent (~250 Torr, 85° C. for 90 minutes) resulted in 81 grams of a thin dark amber oil. The structure of this triazole was confirmed by NMR and LC-MS.

Example 3

Synthesis of Methyl 3-(4-(2-hydroxypropan-2-yl)-1H-1,2,3-triazol-1-yl)propanoate Standard Procedure with Catalyst/Organic Solvent

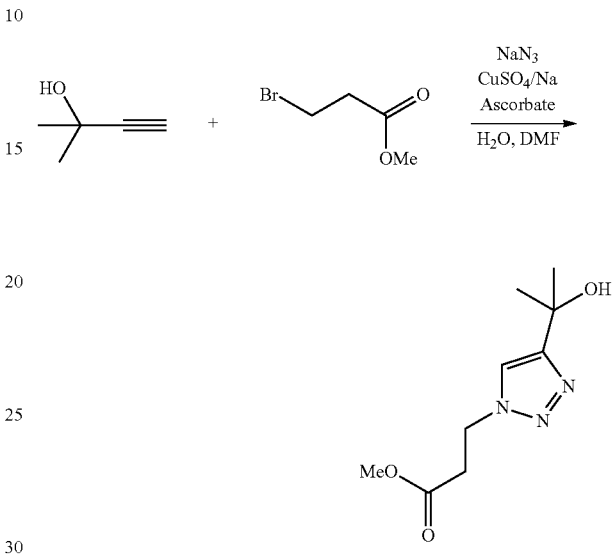

A 1 liter 4-neck round-bottom reaction flask was equipped with a mechanical mixer, reflux condenser, heating mantle, temperature probe and temperature controller. The flask was charged with water (162.4 grams), sodium azide (40.0 grams, 0.6153 mol), sodium ascorbate (8.2 grams, 0.0414 mol), and copper sulfate (2.2 grams, 0.0138 mol). The mixture was stirred to dissolve solids, resulting in a clear dark brown solution. N,N dimethylformamide (DMF, 162.4 grams) was added and the solution became a turbid orange dispersion. No observable change occurred with the addition of methyl-3-bromopropionate (23.1 grams, 0.1383 mol). However, the reaction became a light gold color when 2-methyl-3-butyn-2-ol (17.45 grams, 0.2075 mol) was added as the last reactant. The dispersion was heated with mixing for 20 hours at ~70° C. The opaque dark brown reaction was discharged to a separatory funnel to cool. After the addition of dichloromethane, water, and brine (200 ml each), the reaction separated to a dark red aqueous phase over a light brown organic phase. The organic phase was collected and set aside. Three extractions each using 200 mL of dichloromethane were performed on the aqueous phase of the reaction. More brine was added as needed to aid in phase separation. The dichloromethane solution from the first extraction was light yellow and hazy while the final was clear and colorless. The initial organic phase and the extractions were combined and washed three times each with 250 ml of water. After washing, the hazy golden yellow organic phase was dried over 10 grams of magnesium sulfate. The mixture was filtered and the final solution was concentrated on a roto-evaporator at about 80° C. The product was collected as a clear red-orange low-viscosity oil. The structure of this triazole was confirmed by NMR and LC-MS.

Example 4

Synthesis of methyl 3-(4-(2-hydroxypropan-2-yl)-1H-1,2,3-triazol-1-yl)propanoate Green Procedure—No Catalyst/Organic Solvent

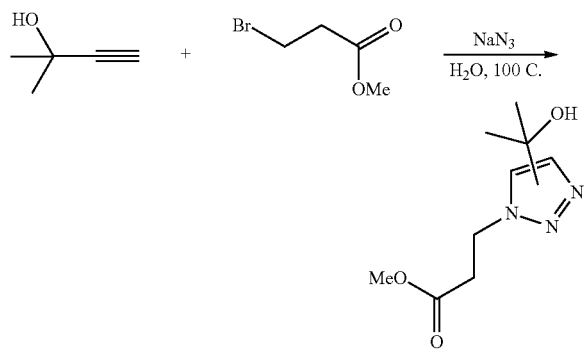

A 500 ml 4-neck round-bottom reaction flask was equipped with a mechanical mixer, reflux condenser, hot oil bath, temperature probe and temperature controller. The flask was charged with water (85 grams), sodium azide (20.0 grams, 0.0.3076 mol), methyl-3-bromopropionate (46.71 grams, 0.2797 mol), and 2-methyl-3-butyn-2-ol (23.53 grams, 0.2797 mol). A mild air-flow was applied to flush the flask for the course of the reaction. The resulting dispersion was placed in a hot oil bath and heated to reflux with mixing for 24 hours at about 94 to ~102° C. The hazy gold-brown reaction solution was discharged to a separatory funnel to cool. Water (340 ml) was also charged to the funnel. The reaction failed to phase out into separate organic and aqueous layers. Four ethyl acetate extractions of 100 ml each were performed to obtain product from the homogeneous solution. Based on thin-layer chromatography eluted with ethyl acetate, the first two extractions contained product and were combined to form a product solution. The product solution was then washed three times with 200 ml of de-ionized water per wash. The dark gold organic phase was then dried over 10 grams of magnesium sulfate and filtered. Methanol (50 ml) was stirred into the 250 ml ethyl acetate-product solution followed by 15 grams of silica gel. The resulting mixture was stirred for one hour, filtered and then concentrated. The product was collected as a dark brown oil. The structure of this triazole in isomeric forms was confirmed by NMR and LC-MS.

Example 5

Synthesis of methyl 3-(4-(prop-1-en-2-yl)-1H-1,2,3-triazol-1-yl)propanoate

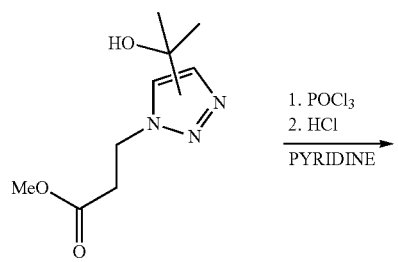

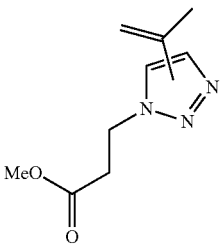

A 100 mL 4-neck round bottom reaction flask was equipped with a magnetic stir bar, thermometer, temperature controller, condenser, oil bath and salt/ice bath. The flask was charged with methyl 3-(4-(2-hydroxypropan-2-yl)-1H-1,2,3-triazol-1-yl)propanoate (5.0 grams, 0.0235 mol) and pyridine (48.9 grams, 0.6182 mol) at room temperature. The resulting clear gold solution was mixed for 5 minutes. A slow-addition funnel charged with POCl₃ was mounted on the flask. The flask and contents were chilled to −7° C. in the salt/ice bath. POCl₃ (7.2 grams, 0.0470 mol) was added drop-wise while a reaction temperature</=10° C. was maintained. At this scale, the addition lasted ~0.5 hrs and the reaction temperature ranged from −7 to 10° C. By the end of the addition, the contents of the flask changed from a clear gold solution to a thick gold-yellow slurry. The reaction flask was then placed into a hot oil bath and the contents were mixed and heated to reflux for 2 hours at a reaction temperature~110 to 122° C. By the end of the heating process, the reaction was a clear red-brown solution, which was allowed to cool over night. During cooling, crystals formed on the bottom of the flask. The contents of the flask were then discharged to a separatory funnel filled with ice. [Beware of heat generated by the dissolution of HCl, a by-product of the reaction.] Approximately 200 ml each of water and methylene chloride were added to the funnel after cooling to promote separation of the aqueous and organic layers. However, the darkness of the layers precluded observation of the separation. The reaction solution was then stripped of pyridine (and methylene chloride) on the roto-evaporator at 80-90° C. Once again, 200 ml each of both water and methylene chloride were added, the layers were observed to separate and the organic layer was collected. The organic layer was then washed with 500 ml of 1M hydrochloric acid solution, which changed the organic solution from dark brown to clear amber. The acid wash was followed by a 300 ml saturated sodium bicarbonate wash. The reaction solution was then dried over 10 grams of magnesium sulfate, filtered and concentrated on a roto-evaporator. The product was collected as a dark brown opaque oil and the structure was confirmed by both NMR and HPLC.

Example 6

Synthesis of 1-hydroxyethyl-1,2,3-triazol-4-yl)propan-2-ol

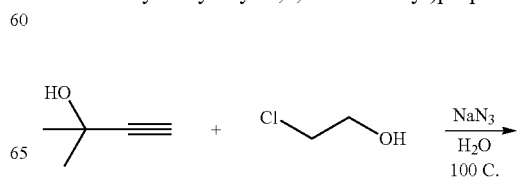

-continued

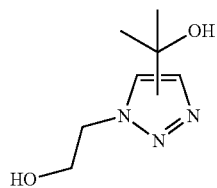

A 500 ml 4-neck round-bottom reaction flask was equipped with a mechanical mixer, reflux condenser, heating mantle, temperature probe and temperature controller. The flask was charged with water (125 grams), sodium azide (39.97 grams, 0.6148 mol), 2-methyl-3-butyn-2-ol (47.01 grams, 0.5589 mol) and 2-chloroethanol (45.0 grams, 0.5589 mol). A continuous air purge was applied to sweep the contents of the flask. The set point of the internal temperature controller was set to about 110° C. and the contents were mixed vigorously at 400 rpms. The reaction was heated to reflux and maintained at a temperature between 92 and 105° C. Reaction conversion was monitored via thin-layer chromatography using an ethyl acetate/hexane solvent system of 4/1 by volume, respectively. After 24 hours of refluxing, the reaction color changed from a cloudy light gray to a hazy dark gold color. The reaction was stopped and the bulk of the water was removed via roto-evaporation (2 hours @ 85-90° C. and ~250 Torr). The crude product mixture was dissolved in 750 ml of acetone, which promoted precipitation of salts. The salts were filtered from the product solution three times as they continued to form. When clear, the final solution was then poured through 55 grams of silica gel constructed as a pad in a Buchner funnel. The product was concentrated on a roto-evaporator and collected as a clear gold oil. The structure of this triazole was confirmed by NMR and LC-MS.

Example 7

Synthesis of 2-(4-prop-1-en-2-yl)-1H-1,2,3-triazol-1-yl)ethanol

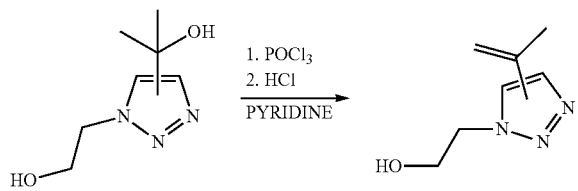

A 1 L 4-neck round bottom reaction flask was equipped with a mechanical stirrer, thermometer, temperature controller, condenser, oil bath and salt/ice bath. The flask was charged with 1-hydroxyethyl-1,2,3-triazol-4-yl)propan-2-ol (40.0 grams, 0.2336 mol) and pyridine (486 grams, 6.1437 mol) at room temperature. The cloudy gold-yellow solution was mixed for 5 minutes. A slow-addition funnel charged with POCl₃ was mounted on the flask. The flask and contents were chilled to about 1° C. in the salt/ice bath. POCl₃ (71.64 grams, 0.4672 mol) was added drop-wise while maintaining a reaction temperature</=10° C. At this scale, the addition lasted 1.25 hrs and the reaction temperature ranged from about −5 to 7° C. By the end of the addition, the contents of the flask changed to an orange solution with white salts. The reaction flask was then placed into a hot oil bath and the contents were mixed and heated to reflux for 2 hours at a reaction temperature~120° C. By the end of heating, the reaction was a clear dark brown solution, which was allowed to cool. The contents of the flask were then discharged to a 2 L separatory funnel filled with ice. [Beware of heat generated by the dissolution of HCl, a by-product of the reaction.] The reaction solution was then extracted twice with 250 ml each of ethyl acetate. The ethyl acetate fractions both phased-out well over the aqueous layers within five minutes. The extractions were then combined and washed four times with 500 ml each of 1M HCl. By the end of the fourth wash, the pH of the washes had dropped from 6 to 0, indicating that most of the pyridine had been removed. The acid washes were followed by a 300 ml saturated sodium bicarbonate wash. The hazy gold reaction solution was isolated and dried over 10 grams of magnesium sulfate, filtered and concentrated on a roto-evaporator at 85° C. The product was collected as a clear gold oil and the structure was confirmed by NMR and HPLC.

Example 8

Synthesis of 2-(1-(2-(2-hydroxyethoxy)ethyl)-1H-1, 2,3-triazol-5-yl)propan-2-ol

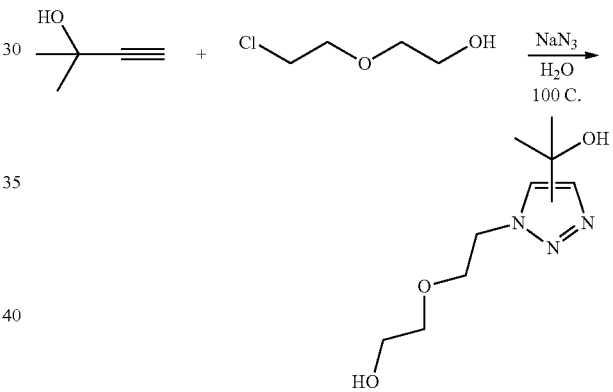

A 1 L 4-neck round-bottom reaction flask was equipped with a mechanical mixer, reflux condenser, heating mantle, temperature probe and temperature controller. The flask was charged with water (214 grams), sodium azide (57.4 grams, 0.8830 mol), 2-methyl-3-Butyn-2-ol (75.5 grams, 0.0.8028 mol) and 2-(2-chloroethoxy)-ethanol (100.0 grams, 0.8028 mol). A continuous air purge was applied to sweep the contents of the flask. The set point of the internal temperature controller was set to 110° C. and the contents were mixed vigorously (400 rpms). The reaction was heated to reflux and maintained at a temperature between 92 and 108° C. Reaction conversion was monitored via thin-layer chromatography using an ethyl acetate/hexane solvent system of 4/1 by volume, respectively. After 24 hours of heating, the reaction color changed from a cloudy light gray to a hazy dark gold color. The bulk of the water was removed via roto-evaporation for ~2 hours at 85-90° C. and ~250 Torr. The crude product mixture was dissolved in 700 ml of acetone, which promoted precipitation of salt. The salts were filtered from the product solution three times as they continued to form. The final clear solution was then poured through 55 grams of silica gel constructed as a pad in a Buchner funnel. The product was concentrated on a roto-evaporator and collected as a clear gold oil. The structure of this triazole was confirmed by NMR and LC-MS.

Example 9

Synthesis of 2-(2-(5-(prop-1-en-2-yl)-1H-1,2,3-triazol-1-yl)ethoxy)ethanol

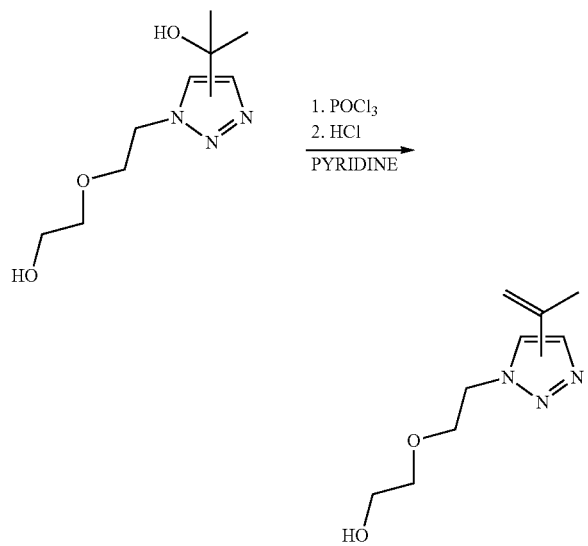

A 1 L 4-neck round bottom reaction flask was equipped with a mechanical stirrer, thermometer, temperature controller, condenser, oil bath and salt/ice bath. The flask was charged with 2-(1-(2-(2-hydroxyethoxy)ethyl)-1H-1,2,3-triazol-5-yl)propan-2-ol (40.0 grams, 0.1859 mol) and pyridine (386.7 grams, 4.8892 mol) at room temperature. The cloudy gold-yellow solution was mixed for 5 minutes. A slow-addition funnel charged with POCl₃ was mounted on the flask. The flask and contents were chilled to 2° C. in the salt/ice bath. POCl₃ (57.00 grams, 0.3718 mol) was added dropwise while the reaction temperature was maintained at </=5° C. The addition lasted 1.3 hrs and the reaction temperature ranged from about −2 to 2° C. By the end of the addition, the contents of the flask changed to a white mixture. The reaction flask was then placed into a hot oil bath and the contents were mixed and heated to reflux for 3 hours at a reaction temperature ~119° C. By the end of heating, the reaction was a clear dark brown solution. In an effort to remove pyridine before work-up, a Dean-Stark trap was fitted to the reflux condenser whereby 186 ml of a clear and colorless liquid was collected over 30 minutes. The product solution was allowed to cool over night. The following day, the contents of the flask were discharged to a 2 L separatory funnel filled with ice. [Beware of heat generated by the dissolution of HCl, a by-product of the reaction.] The reaction solution was then extracted twice with 250 ml each of ethyl acetate. The extractions were then combined and washed four times with 500 ml each of 1M HCl. By the end of the fourth wash, the solution had dropped from pH 6 to pH 0, thereby indicating that most of the pyridine had been removed. The acid washes were followed by a 300 ml saturated sodium bicarbonate wash. The product solution was isolated and dried over 10 grams of magnesium sulfate, filtered and concentrated on a roto-evaporator at 85° C. The product was collected as a dark brown oil and the structure was confirmed by both NMR and HPLC.

Example 10

Synthesis of 2-(1-(2-(dimethylamino)ethyl)-1H-1,2,3-triazol-5-yl)propan-2-ol

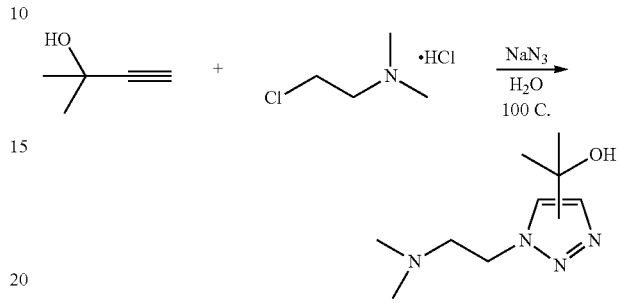

A 2 L 4-neck round-bottom reaction flask was equipped with a mechanical mixer, reflux condenser, heating mantle, temperature probe and temperature controller. The flask was charged with water (464 grams), sodium azide (100 grams, 1.53 mol), 2-methyl-3-butyn-2-ol (117.6 grams, 1.398 mol) and (dimethylamino)ethylchloride.HCl (201.4 grams, 1.398 mol). A continuous air purge was applied to sweep the contents of the flask. The set point of the internal temperature controller was set to 110° C. and the contents were mixed vigorously (400 rpms). The reaction was heated to reflux and was maintained at a temperature between 81 and 103° C. After 24 hours of heating, the reaction color changed from a dark orange to a hazy dark yellow color. The crude product mixture was dissolved in 1000 ml of acetone, which promoted precipitation of salts. Salts were filtered from the product solution three times as they continued to form. The final clear solution was then poured through silica gel constructed as a pad in a Buchner funnel. The product was concentrated on a roto-evaporator and collected as a thick hazy amber oil. The structure of this triazole was confirmed by both NMR and LC-MS.

Example 11

Synthesis of N,N-dimethyl-2-(5-(prop-1-en-2-yl)-1H-1,2,3-triazol-1-yl)ethanamine

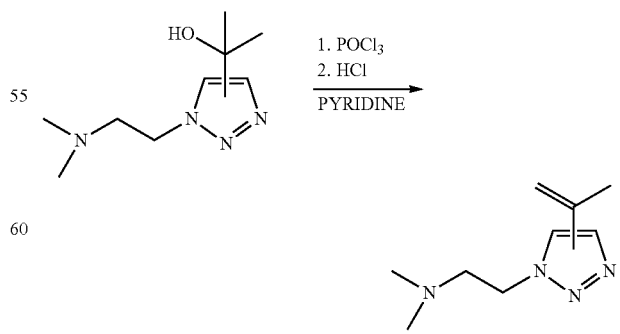

A 1 L 4-neck round bottom reaction flask was equipped with a mechanical stirrer, thermometer, temperature controller, condenser, oil bath and salt/ice bath. The flask was charged with 2-(1-(2-(dimethylamino)ethyl)-1H-1,2,3-triazol-5-yl)propan-2-ol (40 grams, 0.2017 mol) and pyridine (419.6 grams, 5.3047 mol) at room temperature. The solution was mixed for 5 minutes. A slow-addition funnel charged with POCl₃ was mounted on the flask and the contents were chilled in a salt/ice bath. POCl₃ (61.8 grams, 0.4030 mol) was added drop-wise while maintaining a reaction temperature$\leq$/=10° C. The reaction flask was then placed into a hot oil bath and the contents were mixed and heated to reflux for 2 hours at a reaction temperature~120° C. After heating, the reaction was allowed to cool and the contents of the flask were discharged to a 2 L separatory funnel filled with ice [beware of heat generated by the dissolution of HCl, a by-product of the reaction]. The reaction solution was then extracted twice with 250 ml each of ethyl acetate. The extractions were then combined and washed four times with 500 ml each of 1M HCl. By the end of the fourth wash, the pH of the wash dropped from 6 to pH 0, thereby indicating that most of the pyridine had been removed. The acid washes were followed by a 300 ml saturated sodium bicarbonate wash. The reaction solution was isolated and dried over 10 grams of magnesium sulfate, filtered and concentrated on a roto-evaporator at 80° C. The product was collected and submitted for structure confirmation by both NMR and HPLC.

Example 12

Synthesis of poly[1-octyl-4-(prop-1-en-2yl)-1H-1,2,3-triazole]

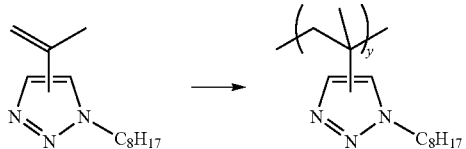

A mixture of 2,2'-azobis-2-methylpropionitrile (27.0 mg, 0.122 mmol) and the triazole monomer (4.00 g, 18.1 mmol) was bubbled with nitrogen at room temperature for at least 10 minutes, and heated at 70° C. for 4 hours. The crude polymerization mixture was then precipitated twice in hexanes. The hexanes were then decanted and the remaining pure polymer was dried under vacuum for 12 hours. The structure of the polymer was confirmed by GPC, NMR, and DSC.

Example 13

Synthesis of poly[1-octyl-4-(prop-1-en-2yl)-1H-1,2,3-triazole-alt-maleic anhydride]

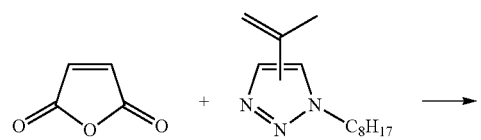

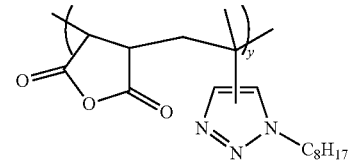

52.5 g Maleic anhydride, 119.0 g triazole monomer, and 214 ml methyl ethyl ketone (MEK) was added into a one-liter five-neck resin kettle, fitted with a Teflon anchor agitator, a nitrogen purge dip tube, a thermocouple, a reflux condenser, and an adapter. The reactor was purged with nitrogen throughout the experiment and heated to 75° C. After the temperature reached 75° C., the reaction mixture was further bubbled with nitrogen for ½ hour. Then 2.4 g of AIBN in 25 ml MEK were added into the kettle. After one hour and two hour, two aliquots of 1.2 g AIBN in 10 ml MEK were charged into the systems respectively. The reaction was continued for another 2 hours, and then the crude polymerization mixture was precipitated twice in methanol/hexanes. The solvents were then removed by filtration and the remaining pure polymer was dried under vacuum for 12 hours. The structure of the polymer was confirmed by GPC, NMR, DSC, and TGA.

Example 14

Synthesis of poly[1-octyl-4-(prop-1-en-2yl)-1H-1,2,3-triazole-alt-maleic diacid]

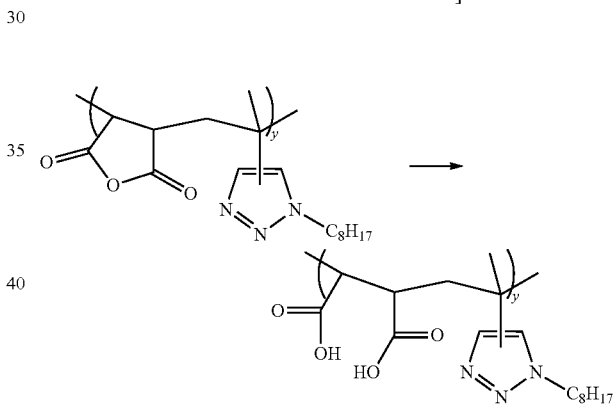

A mixture of 1.0 g of poly[1-octyl-4-(prop-1-en-2yl)-1H-1,2,3-tri azole-alt-maleic anhydride] and 100 ml 0.1 M NaOH aqueous solution was heated at 60° C. for four hours, at which point the mixture became homogenous. The pH of the reaction was then adjusted to pH=7 by using 0.1 M HCL aqueous solution. Adjusting the pH below 5.5 would cause the polymer to precipitate. The structure of the water-soluble polymer was confirmed by GPC, NMR and DLS.

Example 15

Synthesis of poly[1-octyl-4-(prop-1-en-2yl)-1H-1,2,3-triazole-co-N-vinyl-pyrrolidone]

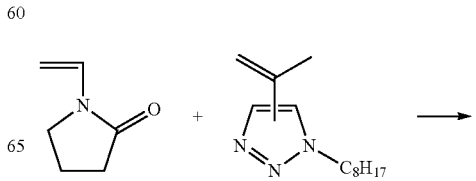

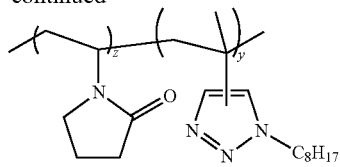

A mixture of 2,2'-azobis-2-methylpropionitrile (120 mg, 0.73 mmol), the triazole monomer (2.70 g, 12.2 mmol), N-vinyl-pyrrolidone (0.30 g, 2.69 mmol), and iso-propanol (4.21 g, 70.0 mmol) was bubbled with nitrogen line for 10 minutes, and heated at 70° C. for 6 hours. The viscous crude polymerization mixture was then precipitated twice in hexanes. The solvents were then removed by filtration and the remaining pure polymer was dried under vacuum for 12 hours. The structure of the polymer was confirmed by GPC, NMR, and DSC.

Example 16

Synthesis of poly[1-octyl-4-(prop-1-en-2yl)-1H-1,2,3-triazole-co-N-vinyl-caprolactam]

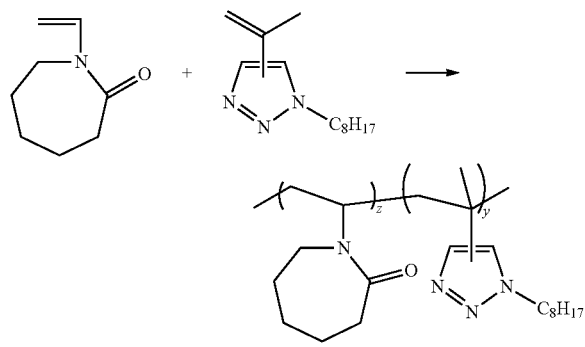

A mixture of 2,2'-azobis-2-methylpropionitrile (40.0 mg, 0.244 mmol), the triazole monomer (0.42 g, 1.90 mmol), N-vinyl-caprolactam and (4.08 g, 29.3 mmol), and ethanol (4.80 g, 104 mmol) was bubbled with nitrogen at room temperature for at least 10 minutes, and heated at 70° C. for 9 hours. The viscous crude polymerization mixture was then precipitated twice in hexanes. The solvents were then removed by filtration and the remaining pure polymer was dried under vacuum for 12 hours. The structure of the polymer was confirmed by GPC and NMR.

Example 17

Synthesis of poly[1-octyl-4-(prop-1-en-2yl)-1H-1,2,3-triazole-co-N,N-dimethylaminoethyl methacrylate]

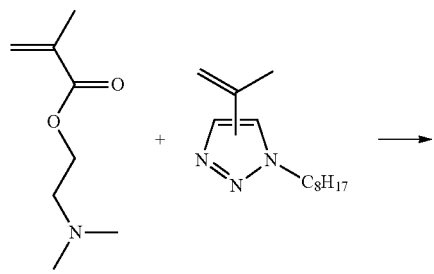

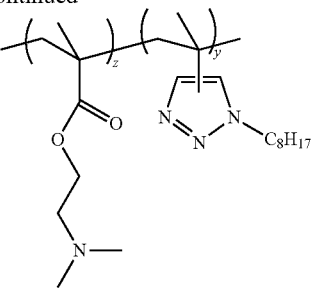

A mixture of 2,2'-azobis-2-methylpropionitrile (31.4 mg, 0.191 mmol), the triazole monomer (0.40 g, 1.81 mmol), and N,N'-dimethylaminoethyl methacrylate (4.00 g, 25.4 mmol) was bubbled with nitrogen line for 10 minutes, and heated at 70° C. for 3.5 hours. The viscous crude polymerization mixture was then precipitated twice in hexanes. The solvents were then removed by filtration and the remaining pure polymer was dried under vacuum for 12 hours. The structure of the polymer was confirmed by GPC and NMR.

Example 18

Synthesis of poly[1-octyl-4-(prop-1-en-2yl)-1H-1,2,3-triazole-co-N,N-dimethylamino-propyl methacrylamide]

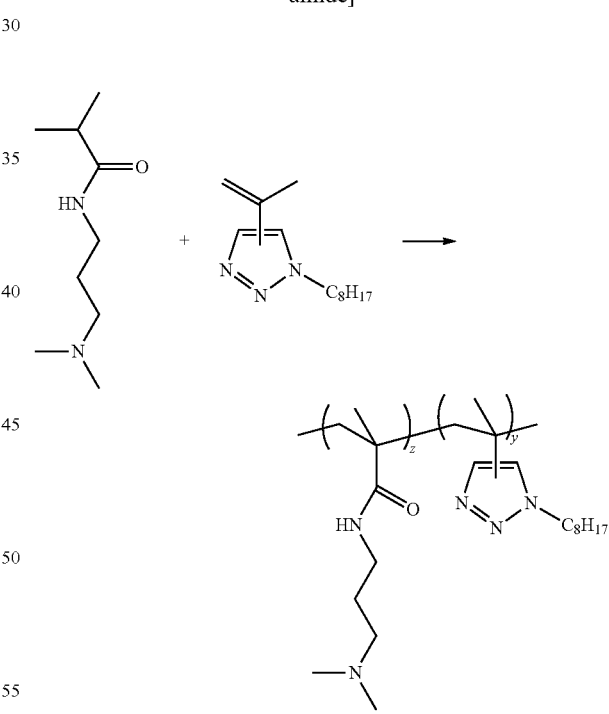

A mixture of 2,2'-azobis-2-methylpropionitrile (30.4 mg, 0.185 mmol), the triazole monomer (0.40 g, 1.81 mmol), and N,N'-dimethylaminoethyl methacrylate (4.00 g, 23.5 mmol) was bubbled with nitrogen at room temperature for at least 10 minutes, and heated at 70° C. for 4.5 hours. The viscous crude polymerization mixture was then precipitated twice in hexanes. The solvents were then removed by filtration and the remaining pure polymer was dried under vacuum for 12 hours. The structure of the polymer was confirmed by GPC and NMR.

Example 19

Synthesis of poly[1-octyl-4-(prop-1-en-2yl)-1H-1,2,3-triazole-co-acrylic acid]

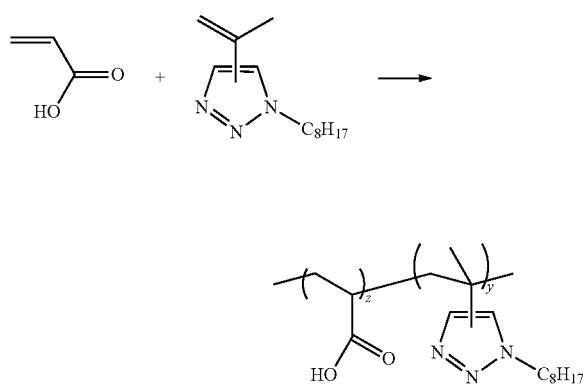

A mixture of 2,2'-azobis-2-methylpropionitrile (32.1 mg, 0.195 mmol), the triazole monomer (0.40 g, 1.81 mmol), and acrylic acid (4.00 g, 55.5 mmol) was bubbled with nitrogen at room temperature for at least 10 minutes, and heated at 70° C. for 1.5 hours. The resulting white solid polymer was then precipitated twice in methanol and dried under vacuum for 12 hours.

Example 20

Synthesis of poly[1-octyl-4-(prop-1-en-2yl)-1H-1,2,3-triazole-co-styrene]

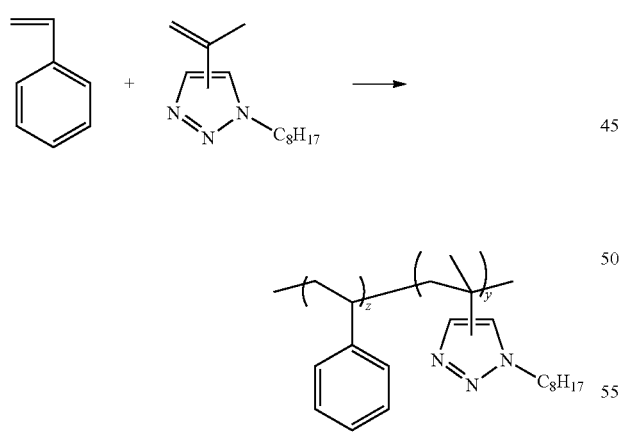

A mixture of 2,2'-azobis-2-methylpropionitrile (30.8 mg, 0.188 mmol), the triazole monomer (0.80 g, 3.62 mmol), and styrene (4.00 g, 38.4 mmol) was bubbled with nitrogen line for 10 minutes, and heated at 70° C. for 7.0 hours. The viscous crude polymerization mixture was then precipitated twice in methanol. The solvents were then removed by filtration and the remaining pure polymer was dried under vacuum for 12 hours. The structure of the polymer was confirmed by GPC, NMR, and DSC.

Example 21

Synthesis of poly[1-octyl-4-(prop-1-en-2yl)-1H-1,2,3-triazole-co-methyl acrylate]

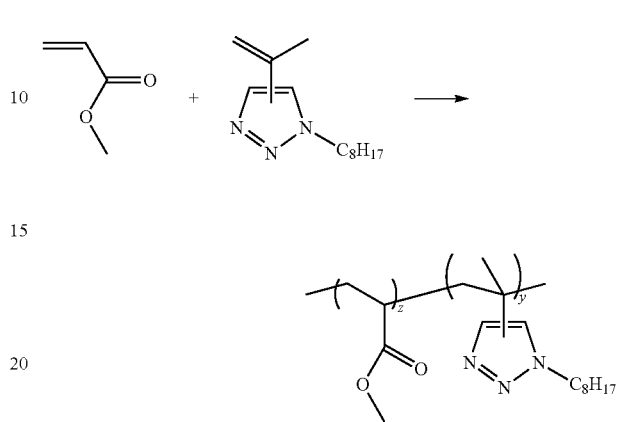

A mixture of 2,2'-azobis-2-methylpropionitrile (30.5 mg, 0.186 mmol), the triazole monomer (0.80 g, 3.62 mmol), and methyl acrylate (4.00 g, 46.5 mmol) was bubbled with nitrogen at room temperature for 10 minutes, and heated at 70° C. for 3.0 hours. The viscous crude polymerization mixture was then precipitated twice in methanol. The solvents were then removed by filtration and the remaining pure polymer was dried under vacuum for 12 hours. The structure of the polymer was confirmed by GPC, NMR, and DSC.

Example 22

Synthesis of poly[1-octyl-4-(prop-1-en-2yl)-1H-1,2,3-triazole-co-methyl methacrylate]

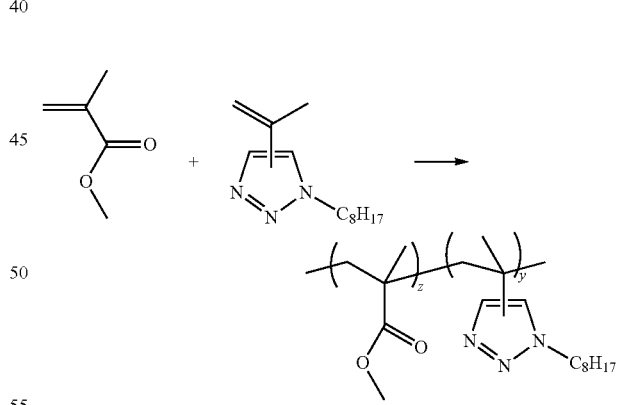

A mixture of 2,2'-azobis-2-methylpropionitrile (34.7 mg, 0.212 mmol), the triazole monomer (0.80 g, 3.62 mmol), and methyl methacrylate (4.00 g, 40.0 mmol) was bubbled with nitrogen line for 10 minutes, and heated at 70° C. for 3.0 hours. The viscous crude polymerization mixture was then precipitated twice in methanol. The solvents were then removed by filtration and the remaining pure polymer was dried under vacuum for 12 hours. The structure of the polymer was confirmed by GPC, NMR, and DSC.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. An alcoholic mixture having the structure:

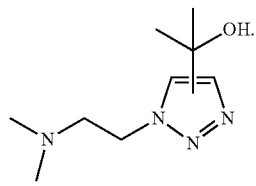

2. An adhesive, coating, encapsulation, personal care, oilfield, membrane, agricultural, or cleaning composition comprising an alcoholic mixture having the structure:

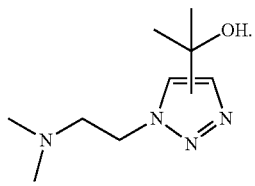

3. An electronic, electrical, opto-electronic, or photo-electronic composition comprising an alcoholic mixture having the structure:

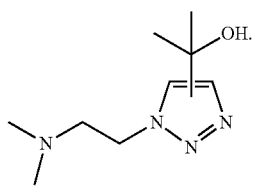

* * * * *